United States Patent [19]

Smith et al.

[11] Patent Number: 5,161,889
[45] Date of Patent: Nov. 10, 1992

[54] HEAT TRANSFER RATE TARGET MODULE

[75] Inventors: Donald P. Smith, Dallas; Jarald E. High, Grand Prairie; John R. Norris, Plano, all of Tex.

[73] Assignee: Patentsmith II, Inc., Dallas, Tex.

[21] Appl. No.: 709,717

[22] Filed: Jun. 3, 1991

[51] Int. Cl.$^5$ ............................................ G01K 17/00
[52] U.S. Cl. ........................................ 374/29; 374/43; 219/399; 426/465
[58] Field of Search ................ 374/29, 30, 33, 43, 374/44; 219/394, 393, 400, 398, 399; 99/328, 333, 372; 426/465

[56] References Cited

U.S. PATENT DOCUMENTS

| | | | |
|---|---|---|---|
| 3,372,587 | 3/1968 | Nanigian | 374/30 X |
| 3,725,645 | 4/1973 | Shevlin | 99/328 X |
| 4,364,308 | 12/1982 | John et al. | 99/372 X |
| 4,553,852 | 11/1985 | Derderian | 374/30 X |
| 4,607,961 | 8/1986 | Wynnyckyj et al. | 374/30 |
| 4,831,238 | 5/1989 | Smith et al. | 219/400 |

OTHER PUBLICATIONS

Baker's Super M.O.L.E. Thinline, Electronic Controls Design, Inc., Rev. May 1990.
ECD Super M.O.L.E. Applications, Electronic Controls Design, Inc. (no date).
Channel Hand-Held Printing Datalogger with Memory, Electronic Controls Design, Inc., Rev. Apr. 1990.
Super M.O.L.E. Turns Dough into Dollars, Electronic Controls Design, Inc. (no date).
Who We Are, Electronic Controls Design, Inc. (no date).

Primary Examiner—William A. Cuchlinski, Jr.
Assistant Examiner—G. Bradley Bennett
Attorney, Agent, or Firm—Crutsinger & Booth

[57] ABSTRACT

The invention is an apparatus and method for measuring the heat transfer and the rate of heat transfer in thermal exchange processes such as food processing, thermosetting of plastics, and freezing processes. The apparatus comprises a target module and a data recording module. The target module comprises a target having a known mass and known thermal characteristics. The black body edge effects of the target are minimized by an edge shield positioned adjacent to the target. The edge shield is physically separated from the target so that conductive heat transfer between the two elements is minimized. The edge shield supports the target such that at least one surface of the target is exposed to the surrounding environment. A temperature sensor measures the change in temperature of the target. The data recording module may be insulated so that the calorimetric data may be recorded in extreme temperature environments.

29 Claims, 7 Drawing Sheets

HEAT TRANSFER RATE TARGET MODULE

FIELD OF THE INVENTION

The invention generally relates to an apparatus for measuring and recording the temperature and heat transfer rate in heat transfer equipment such as heaters, ovens, refrigerators, and freezing apparatus. More particularly the invention relates to a device for measuring and recording heat transfer rates over time in single or multiple zone ovens and freezing apparatus.

BACKGROUND OF THE INVENTION

Though the temperature and time of heating and cooling processes are critical factors in the chemical and food processing industries, these two factors only provide partial information about heat transfer.

Taking the food processing industry as an example, a baker may prepare a batch of bread dough, divide it into two portions, and bake the two portions in different ovens at the same temperature and for the same time. Even if the design of each of the ovens is similar, the resulting bread products may be very different. One loaf might be light and moist on the inside and golden brown on the outside, yielding a very pleasant aroma. The other might be heavy and dry with a burnt crust, yielding a biting aroma. Most bakers have experienced the frustration of learning by trial and error the particular characteristics of each oven. Similar difficulties are encountered with cake, pizza, pie, quiche, and every other type of baked food product.

The problems of defining the characteristics of ovens and freezers is not limited to the food industry. Thermosetting of plastics or drying of paints, for example, can be accomplished in an oven or other heating apparatus. Freezing processes, particularly flash freezing processes, are impossible to fully characterize with the factors of time and temperature alone.

Most commercial baking ovens heat a food product by a combination of radiant and convection heating. Radiant heat transfer varies in proportion to the distance from the source to the product cubed or raised to the third power. Convection heat transfer rate varies with air velocity and air flow conditions, such as impingement. Temperature is only one factor.

Ovens with computer programs which vary the form or intensity of energy applied during a baking cycle need more analysis than just a temperature-time profile. A practical and very major problem in the development of baking profiles of food ovens is that the foods change during baking in unpredictable ways, making their use as "standards" difficult, if not impossible. A long felt need exists for a method and apparatus to standardize heat transfer processes. A long felt need also exists for an accurate method to record both the temperatures and the relative effectiveness of the process temperatures in heating or cooling.

SUMMARY OF THE INVENTION

The apparatus of the invention generally comprises a target module and a data recording module.

The target module generally comprises at least one target and at least one edge shield. The target is formed of a material that has a known mass and known thermal characteristics. At least one surface of the target may be exposed to heat energy input within heat exchange equipment. In a preferred embodiment of the invention, the target is formed of pure aluminum. The target measures radiative, conductive, and convective heat transfer between the target and the surrounding atmosphere within the heat exchange equipment.

Edge effects, caused by changes in emissivity of black body radiation due to the changing shape of the target at the edges of the target, are eliminated with an edge shield. Edge effects are also caused by changes in the shape of the target that disturb the normal heat transfer to the target. The edge shield is positioned adjacent to the target such that the target and edge shield present a substantially uniform surface that can be exposed to heat energy input. An air gap thermally insulates the target from the edge shield so that the target may be used as an accurate heat sink for the calorimetric measurement of heat transfer and to accurately indicate quantities of absorbed or evolved heat at critical times during the production or processing of a product.

The target has a temperature sensor to measure the temperature of the target. The change in temperature, combined with the known mass and thermal characteristics of the target, allows the heat transfer and the rate of heat transfer to and from the target to be accurately quantified. The target module may also include a temperature sensor to measure the temperature of the atmosphere surrounding the target module. In a preferred embodiment of the invention, the temperature sensors are thermocouples.

The temperature sensors are connected to the data recording module. The leads of the temperature sensors may be connected to the data inputs of the data recording module by any appropriate means. In a preferred embodiment, the temperature data is electronically transferred with lead wires to the data recording module. The lead wires may be thermally or otherwise protected with a connecting tube. The tube may also serve to physically connect and support the target module near the data recording module. But the temperature data may also be relayed to a remote data recording module by radio, for example.

The data recording module generally comprises a data logger. The data logger comprises a clock, temperature data inputs, a data recording device, and a power supply. The clock determines at what intervals data should be accumulated. The data recording device may be analog or digital. If the data recording device is digital, such as a computer chip, then if the temperature data is provided in analog, the data logger requires an analog to digital converter. The power supply is a battery or any other suitable electrical source.

The data recording module may be located near the target module or may be located remote from the target module. The data recording module should not be located so close to the target module that the calorimetric properties of the data recording module effect the heat transfer exchange between the target module and the surroundings. In a preferred embodiment, a data recording module includes a thermally insulated case so that the data logger may be insulated from extreme temperatures while accompanying the target module into the environment for which the heat exchange rate is to be measured.

It is an object of the invention to provide an apparatus for measuring the rate of heat transfer in heat transfer process. It is another object of the invention to provide an apparatus for measuring the profile of the rate of heat transfer across time in heat transfer processes. Such heat transfer processes include baking processes in the food processing industry and thermoplastic setting or flash freezing in the chemical process industry. It is yet another object of the invention to provide a method for measuring the heat transfer and heat transfer rates in heat exchange processes.

BRIEF DESCRIPTION OF THE DRAWING

Drawings of a preferred embodiment of the invention are annexed hereto so that the invention may be better and more fully understood, in which.

Numeral references are employed to designate like parts throughout the various figures of the drawings.

DESCRIPTION OF PREFERRED EMBODIMENTS

After describing the cooperation of parts of preferred embodiments of the heat transfer rate target module, the operation of the apparatus will be described in detail.

Figure 1:
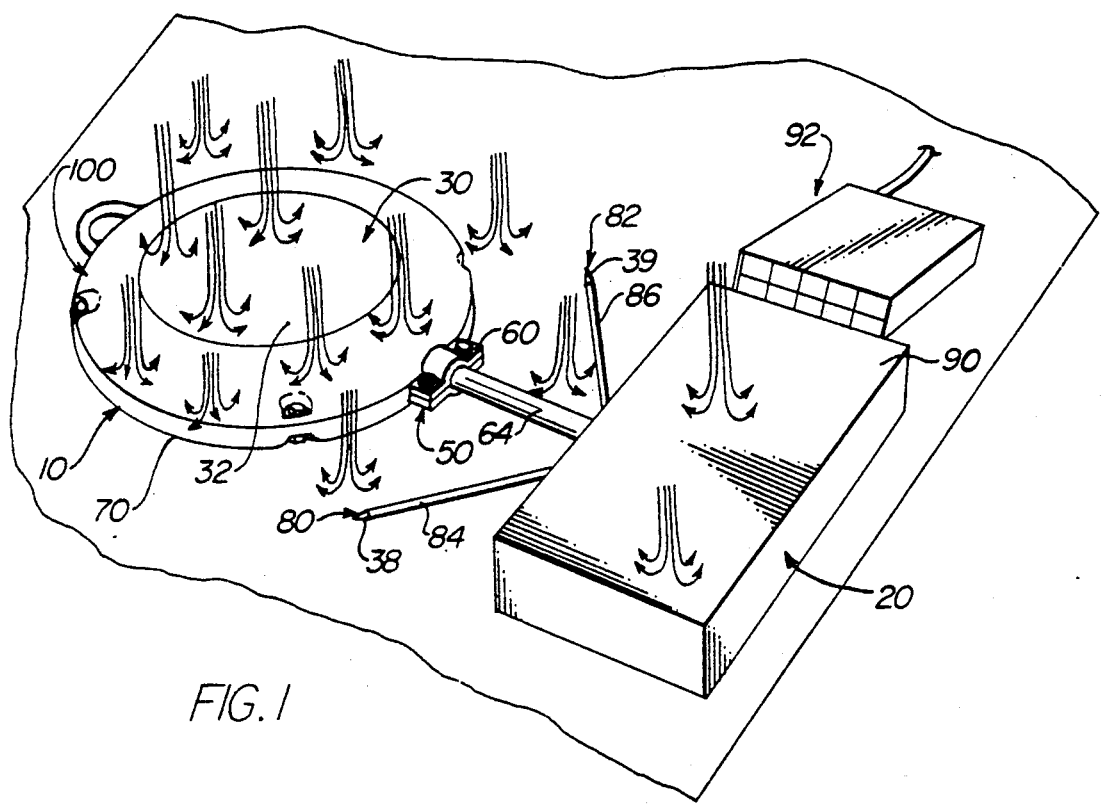
FIG. 1 is a perspective view of the top of a preferred embodiment of the heat transfer rate target module diagrammatically illustrated on a conveyor belt in a hot air impingement oven.
Figure 2:
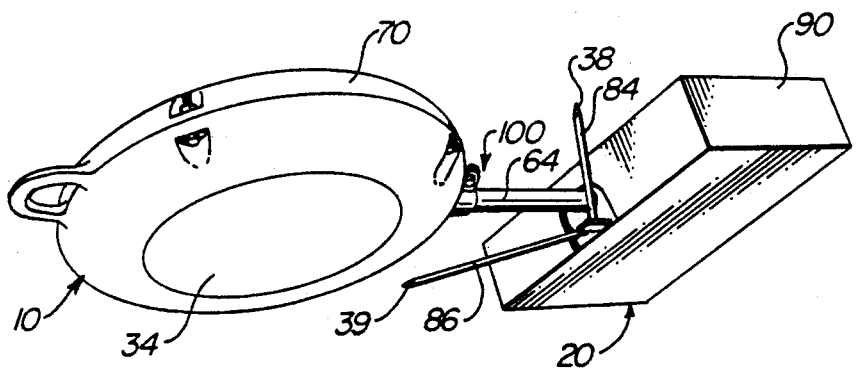
FIG. 2 is a perspective view of the bottom of the heat transfer rate module.

Referring now to FIGS. 1 and 2 of the drawing, the numeral 100 generally designates a heat transfer rate target module comprising a target module 10, a data recording module 20, and a target mounting assembly 50.

Smith et al. U.S. Pat. No. 4,831,238 discloses a high volume forced convection tunnel oven which includes a plurality of spaced cooking compartments through which a conveyor transports food products. An air distribution chamber is formed in an upper portion of each cooking chamber and is vertically spaced from the conveyor. A blower draws air from the cooking compartment and discharges air into the air distribution chamber in a plane generally parallel to the conveyor. A pair of plenums in the cabinet adjacent one edge of the conveyor deliver air from the distribution chamber to a plurality of air dispensing ducts communicating with the plenums on opposite sides of the conveyor for dispensing air onto opposite sides of the conveyor.

The oven disclosed in Smith et al., U.S. Pat. No. 4,831,238 incorporates dampers which are adjustable to provide independent adjustment of air flow through spaced upper air dispensing ducts relative to each of the other air dispensing ducts and to provide adjustment of flow from each of the lower air dispensing ducts relative to each of the other lower dispensing ducts. A gate is provided for adjusting flow of air from the air chamber into upper and lower plenums while the dampers are manipulated for adjusting air flow through individual ducts above and below the conveyor. Thus, the flow of air or other heat transfer media delivered in streams from upper and lower air dispensing ducts is adjustable to control the flow of temperature controlled air which impinges against upper and lower surfaces of a product carried by a conveyor through the oven.

The heat transfer rate target module 100 may be used to calibrate the various components of the oven to produce precisely prescribed rates of heat transfer to upper and lower surfaces of a food product during several stages of a baking or other food processing operation.

As will be hereinafter more fully explained, the heat transfer rate target module 100 is a convenient device consisting of a carefully standardized heat sink module and a self contained recorder which can be placed along with products passing through any heating and cooling process to accurately record temperatures and heat transfer rates over time.

The heat transfer rate monitor 100 measures the effective heat transfer coefficient, h, in BTU/(hr.) (sq. ft.) (°F), of any oven or, cooler. The concept has proven very valuable in the design, development, engineering, and selection of appropriate ovens or cooling devices for a variety of products. Operations control and maintenance analysis values should be evident.

The Target Module

The target module 10 comprises a target 30 and an edge shield 70 configured to measure heat transfer rates from two generally opposite directions simultaneously but separately. For convenience of description, and not by way of limitation, the two opposite directions are referred to as the top and the bottom of the target module 10 because the target module 10 is usually oriented in an oven as shown in FIG. 1. However, it should be appreciated that the apparatus may be physically rotated or moved in any direction.

Figure 3:
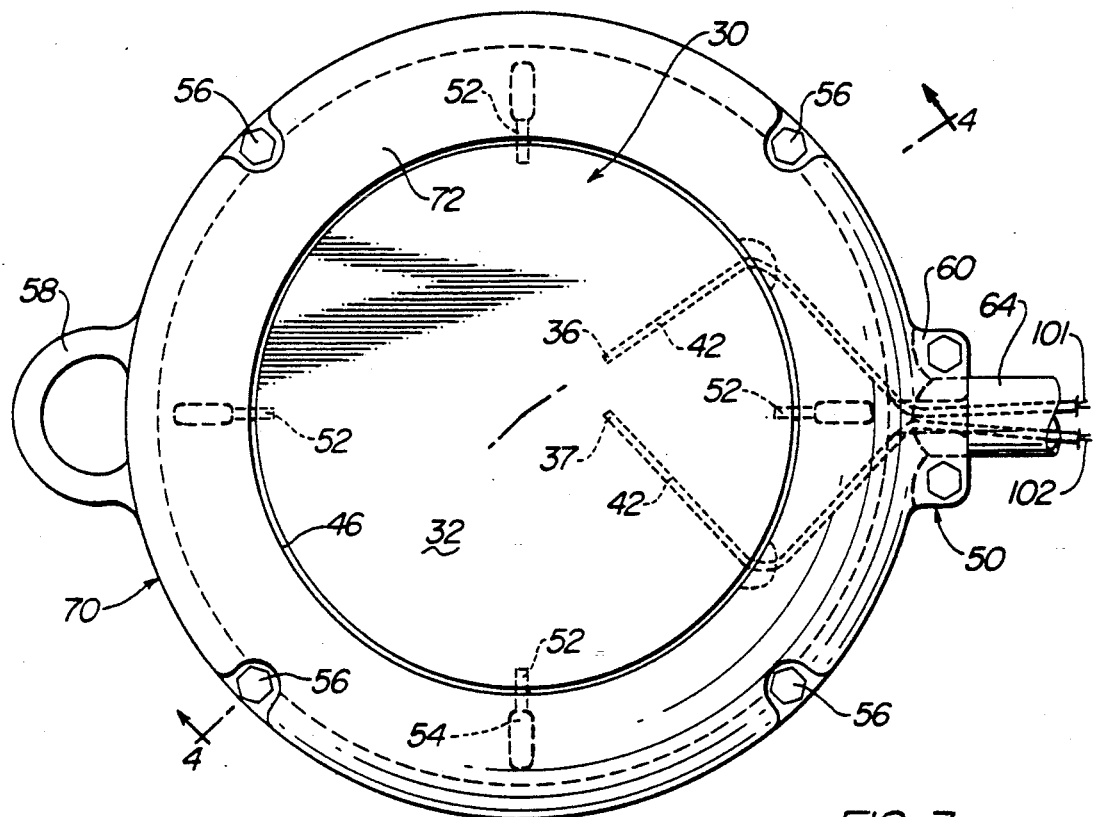
FIG. 3 is a top plan view of a target assembly.
Figure 4:
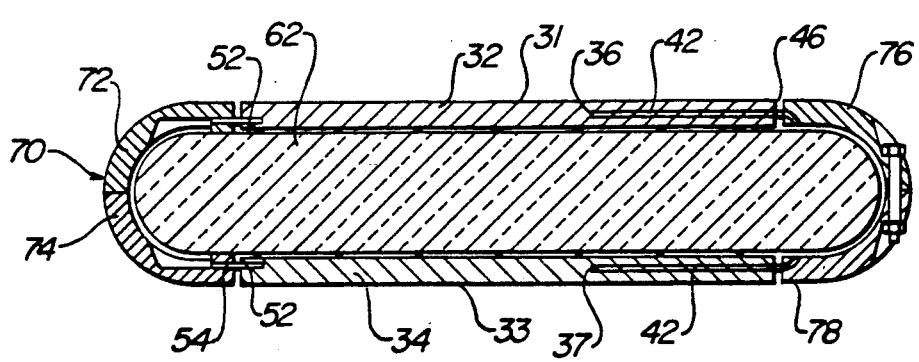
FIG. 4 is a cross-sectional view taken along line 4—4 of FIG. 3.

In the embodiment illustrated in FIGS. 3 and 4, the target module 10 generally comprises a target mounting assembly 50 and two targets 30, for convenience specifically referred to as top target 32 and bottom target 34. The target mounting assembly 50 generally comprises insulating material 62 and two edge shields 70, where necessary specifically referred to as top edge shield 72 and bottom edge shield 74.

The target 30 is formed of a material that has a known mass and known thermal characteristics, including thermal capacity and thermal conductivity. The target 30 forms a heat sink having at least one surface 31 exposed to heat energy input. At least one surface of the target 30 is exposed to heat energy input within the heat transfer processing equipment (not shown). As will hereinafter be explained in detail, knowing the mass and thermal properties of the target allows the target 30 to be used calorimetrically in order to measure "q," the amount of heat transfer between the heat exchange equipment and the target, and "r," the rate of heat transfer between the heat exchange equipment and the target 30.

The target should have known thermal characteristics, but it preferably should also have high thermal conductivity and be formed of a uniform material so that the target is more likely to remain isothermal, that is, the temperature distribution within the target 30 should be as uniform as possible. These thermal properties are well known for numerous materials, especially pure metals and alloys. In a preferred embodiment of the invention, the target 30 is formed of pure aluminum. Other suitable materials for the target 30 include copper and stainless steel.

The target 30 can measure heat energy from conduction and radiation sources. Conduction is the transfer of heat energy by the short-range interaction of atoms, molecules, or electrons. Conduction includes heat transferred to the target 30 by the process of convection, that is, the combined mechanisms of fluid mixing and conduction, such fluid being for example the atmosphere within a heat exchanging chamber. Convection is one of the most important modes of heat energy transfer in baking processes, especially in natural convection, forced convection, and hot-air impingement ovens. If the target module 10 and the data recording module 20 are sufficiently pressure-tight, the heat transfer rate target module could be used in heat exchange equipment wherein thermal energy is transferred by liquid convection.

In cooling and freezing processes, the temperature difference between the surrounding atmosphere and the process product, which can be simulated with the target module 10, is often less than the difference in heating processes. According to Charles' law (also known as Gay-Lusac's law), all else being equal the atmosphere will be more dense at lower temperatures so convective heat transfer rates may be higher than for higher temperature heat transfer processes.

Radiation is the transfer of heat energy by the process of electromagnetic waves. Radiation incident on a body may be absorbed, reflected, scattered, or transmitted. The more polished or shiny the surface, the greater the proportion of incident radiation that will be reflected and scattered rather than absorbed. All bodies above absolute zero temperature radiate energy. A heated body loses energy at a rate dependent on the mass, shape, and particularly the temperature of the body. The ratio of energy being absorbed and energy being emitted will be the rate of change in temperature of a body.

Thermal radiation from a heated body is best understood in terms of an ideal black body or ideal radiator. The black body absorbs all the radiation incident on its surface. Theoretically, the nature and intensity of the radiation the black body emits are determined only by its temperature.

The ratio of the total radiating power of a real surface to that of an ideal black body surface at the same temperature is called the emissivity. The fraction of radiation incident on a surface that is absorbed by the material is called the absorptivity. According to Kirchhoff's law, the emissivity and absorptivity of a surface of a body in surroundings at the same temperature are equal. But when the surface of the body and its surroundings are at different temperatures, the emissivity and absorptivity of the surface of the body are not equal, and heat energy is transferred between the boy and its surroundings.

The gain or loss of heat energy can be detected as a change in temperature. Given the known mass and the known thermal capacity of the material, and assuming that the temperature of the material is uniform throughout the mass of the material, the change in temperature can be used to calculate the heat energy transfer, q, in Equation 1 as follows:

$$q = (\text{mass})(\text{thermal capacity})(\Delta \text{ temperature}) \quad \text{Eq. 1}$$

For many heat exchange processes, the heat exchange per unit area is a more useful type of information, as will be hereinafter explained in more detail. For an isothermal surface, such as the exposed surface area of the target 30 of the target module 10, the heat energy transfer per unit area of the exposed surface of the target 30, $q_a$, can be calculated according to Equation 2 as follows:

$$q_a = a/\text{area, or}$$

$$q_a = (\text{mass})(\text{thermal capacity})(\Delta \text{ temp})/(\text{area}) \quad \text{Eq. 2}$$

Measuring the heat transfer, q, or heat transfer per unit area, $q_a$, in relation to time can provide the rate of heat transfer. For the purposes of this description, r is the rate of heat transfer per unit surface area of the target 30, which is calculated according to Equation 3 as follows:

$$r = q_a/(\Delta \text{ time}), \text{ or} \quad \text{Eq. 3}$$

$$r = \frac{(\text{mass})(\text{thermal capacity})(\Delta \text{ temp})}{(\text{area})(\Delta \text{ time})}$$

The thermal capacity used in Equations 1-3 is the quantity of heat necessary to produce a unit change of temperature in a unit mass of the material:

$$\text{thermal capacity} = \frac{\text{heat energy}}{(\text{mass})(\Delta \text{ temp})} \quad \text{Eq. 4}$$

Thermal capacity is related to specific heat capacity, where specific heat capacity is the thermal capacity of a material relative to a standard, usually water. It should be pointed out that thermal capacity and specific heat are not constant, but change with temperature. For example, in most baking processes for food, the temperature range is between room temperature up to above 450° F. The thermal capacity of aluminum changes by about 10-15% over this temperature range. The varying heat capacity could be taken into account using calculus mathematics. Heat energy can be expressed in any suitable energy units, such as calories, BTU, joules, etc. Similarly, mass, temperature change, surface area, and time can be in any convenient units of measurement.

The accuracy of these calorimetric calculations depends on the assumption that the target material is isothermal. But as previously mentioned, the shape of a heated body has some impact on how it loses heat energy to its surroundings by the process of radiation. A non-uniform surface radiates black body energy non-uniformly, interacts with convection currents non-uniformly, and absorbs radiated energy non-uniformly. Therefore, a non-uniform surface would cause a temperature gradient in an ideal black body. The edge effects are greater in a real body, such as the target 30. Furthermore, a real body does not perfectly absorb conductive and radiative energy. Absorption of heat energy is also affected by non-uniformities in the surface of the target 30. For a cylindrical shaped body such as target 30, the resulting temperature gradient would be most pronounced toward the edges of the body, hence the effects can be called edge effects. The best way to eliminate edge effects is to eliminate, or minimize the edges of the target 30.

Therefore, the most important purpose of the edge shield 70 is to substantially eliminate the edges of the target 30. Another purpose of the edge shield 70, particularly when incorporated into the target mounting assembly 50, is to orient a surface of the target in the desired direction and to insulate the other surfaces of the target from heat exchange in other directions. As will hereinafter be explained in more detail, the target mounting assembly 50 causes the target to absorb heat from the direction of the exposed surface of the target and the edge shield 70 causes the target to maintain a uniform temperature substantially without variations caused by edge effects.

In a preferred embodiment of the invention shown in FIGS. 1-4 of the drawing, the target 30 is generally cylindrical or plate shaped about six (6) inches in diameter and one-quarter (¼) inch high. Though a rectangular or other multi-sided shape could be employed, the cylindrical shape is preferred because the number of non-uniformities in the surface are few. For most applications the thickness of the target 30 should be small so that the target 30 will respond rapidly to heat energy exchange. The surface area and the thickness of the target 30 can be adjusted to simulate the product going through the heat exchange process. The preferred embodiment of the target 30 is suitable for most baked food products. An alternative embodiment for the target 30 will hereinafter be described in detail.

The edge shield 70 preferably has a ring-like shape. The edge shield 70 preferably has the same thickness and is formed of the same material as the target, so that the edge shield 70 heats or cools at approximately the same rate as the target 30. The target 30 in combination with the edge shield 70 should present a substantially uniform surface to the heat exchanging environment. The shape and material, and the position of the edge shield 70 adjacent to the target 30 reduces any edge effects in heating or cooling at the edges of the target 30. But as will hereinafter be explained in more detail, it is important that there is minimal physical contact between the target 30 and the edge shield 70, that is, there should be a small gap 46 between the two.

The edge shield 70 preferably has rounded surfaces, such as rounded surfaces 76 and 78 best shown in FIG. 4, at the outside edge of the edge shield 70, that is, farthest from the target 30. The rounded surfaces 76 and 78 minimize the edge effects of the edge shield 70, such as edge shields 72 and 74. Edge effects are thereby minimized both by the shape of the rounded surfaces 76 and 78 and the distance of the rounded surfaces 76 and 78 from the targets 32 and 34.

The designed combination of the target 30 and edge shield 70 provides a very accurate heat sink. The temperature of the target 30 is going to be about the same all across the surface of the target 30 including at the edge of the target 30 When the edge effect is substantially eliminated by the edge shield 70, the edges of the target 30 thermally behave like the center of the target 30.

In one preferred embodiment of the invention, the edge shield 70 is made of quarter inch cast aluminum stock, the same material as the target 30. The target 30 is formed from sheet stock aluminum, but the edge shield 70 and target 30 have the same thermal properties, such as thermal capacity and thermal conductivity.

The target 30 and the edge shield 70 should fit very closely adjacent to each other, but there should be a physical gap 46 between the two elements and minimal physical contact. The purpose of the gap 46 is to minimize all heat transfer between the target 30 and the edge shield 70. The target 30 and the edge shield 70 can physically touch at a few points without conductively transferring significant heat across the gap 46. Of course, if the target 30 and the edge shield 70 are welded together, the conductive heat transfer is much more efficient, and the calorimetry of the target 30 would be substantially altered, essentially adding the mass of the edge shield 70 to the target 30.

With a narrow gap 46 the heat transfer between the target 30 and the edge shield 70 is low. Minimal physical contact essentially eliminates direct conductive heat transfer between the target 30 and the edge shield 70. The gap 46 should be much too narrow for any substantial convective energy transfer between the target 30 and the edge shield 70. The thickness of the edge shield 70 is preferably about the same thickness as the target 30, so if the target 30 and the edge shield 70 are at the same temperature, then there should be very little radiative heat flow across the gap 46. The black body radiation of the surface on the target 30 that faces the edge shield 70 across the gap 46 should be substantially absorbed by the edge shield 70. Similarly, the black body radiation of the surface on the edge shield 70 that faces the target 30 across the gap 46 should be substantially absorbed by the target 30. This radiative exchange of energy should substantially cancel out.

Therefore, the gap 46 should be minimal, the tiniest space possible. The gap 46 is preferably between about 1/1000th and 25/1000th of an inch. In a more preferred embodiment, the gap 46 is between about 5/1000th and 10/1000th of an inch (5-10 microns). If a coating is put on the target 30, as will be hereinafter described in detail, the gap 46 becomes more narrow. Sometimes it is necessary to sand the edges of the target 30 to fit the target 30 adjacent the edge shield 70.

As best shown in FIGS. 3 and 4, positioning pins 52 may retain the target 30 adjacent the edge shield 70 with the desired gap 46 therebetween. In the preferred embodiment of the invention, the positioning pins 52 are hollow cylindrical roll pins formed of stainless steel so that they can rotate. The positioning pins 52 may be threaded to screw through a threaded pin bore 54 to adjust the position of the target 30 adjacent the edge shield 70. The positioning pins 52 are preferably hollow so that they have less mass, less thermal capacity, and therefore, less ability to conduct heat between the target 30 and the edge shield 70.

In the preferred embodiment, the target 30 and edge shield 70 are assembled such that they will not easily come apart. As will hereinafter be described in detail, the thermocouple sensors should be replaceable without separating the target 30 and edge shield 70.

Figure 5:
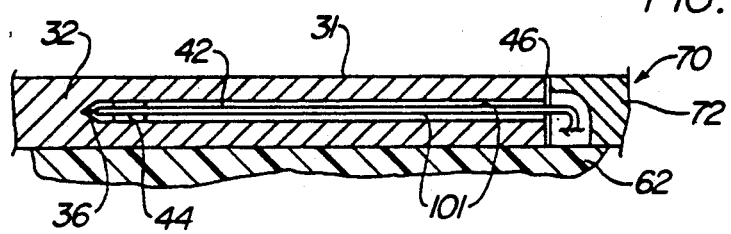
FIG. 5 is an enlarged fragmentary cross-sectional view of a portion of the heat transfer rate target module, illustrating a sensor mounted in a target plate.

At least one temperature sensor should be thermally connected to the target 30. If there are multiple targets 30, such as targets 32 and 34 shown in FIGS. 1-4, there should be at least one temperature sensor for each target. In the preferred embodiment of the invention, the temperature sensor comprises a thermocouple 36. The temperature sensor does not have to be exactly in the center of the target 30, but it should be near the center to minimize any edge effects that the edge shield 70 has not completely eliminated. The thermocouple 36 enters the target 30 through a countersunk hole 42 drilled through the cylindrical wall of the target 30 inside the target 30, as best shown in FIG. 5. The hole 42 extends about a third of the diameter of the target 30, that is, about two (2) inches in the six (6) inch diameter target 30 of the preferred embodiment. The diameter of the hole 42 should be barely large enough so that a thermocouple wire pair can be placed therein.

Physical contact between the end of the thermocouple 36 and the interior body of the target 30 is important. Otherwise if the target module 10 is placed on a surface that is moving or vibrating, such as a conveyer belt, the thermocouple 36 might lose physical contact with the body of the target 30 such that heat of the target 30 would not be efficiently conducted to the thermocouple 36. The thermocouple 36 would give erroneous temperature measurements.

There are several possible construction techniques for firmly affixing the thermocouple 36 against the body of the target 30 at the interior end of the hole 42. One of the simplest involves passing the thermocouple 36 into the hole 42 as far as the thermocouple 36 will go, that is, until the joint end of the thermocouple 36 is touching the body of the target 30 at the interior end of the hole 42. A conductive packing material, such as a piece of tinfoil 44, may be rolled up so that the thin roll of tinfoil 44 has a length about of about one (1) inch. The rolled up tinfoil 44 can be pushed into the hole 42 adjacent to the thermocouple 36 and rammed by a probe tool tightly into the end of the hole 42. The thermocouple 36 is thereby retained tightly in physical contact with the body of the target 30 within the end of the hole 42. If the thermocouple 36 comes apart or otherwise malfunctions, the thermocouple 36 and the piece of tinfoil 44 can be pulled out from the hole 42 by pulling the other ends of the thermocouple wires that remain sticking out of the hole 42 in the target 30. The leads of the thermocouples wires are connected to the data recording module 20, as will be hereinafter described in detail.

The preferred embodiment of the invention shown in FIGS. 1-4 includes two targets 30, top target 32 and bottom target 34, for measuring the heat transfer rate from two opposite directions. More accurate information is obtained from each target if the top target 32 and the bottom target 34 are thermally insulated from heat energy input from the opposite direction. The two targets 32 and 34 and the two edge shields 72 and 74 physically shield each of the targets 32 and 34 from heat energy transfer from the surroundings on the opposite side of the exposed target surface. But unless an insulation material 62 is placed between the two targets 32 and 34, the targets 32 and 34 can exchange heat energy between themselves by the process of conduction, convection, and radiation.

Once the top and bottom targets 32 and 34 have been positioned adjacent the edge shields 72 and 74, respectively, and the thermocouples 36 have been installed in the targets 32 and 34, insulation material 62 may be sandwiched between the targets 32 and 34 before closing the target mounting assembly 50. Thereafter the two edge shields 72 and 74 of the target mounting assembly 50 may be bolted with several nut and bolt assemblies 56 or otherwise removably connected together. The target mounting assembly 50 should be removably connected to provide access to the thermocouples 36 within the targets 32 and 34.

In the preferred embodiment of the invention shown in FIGS. 1-4, the edge shields 72 and 74, have a handling ring 58 adapted to help handle the target module 10, which may be extremely hot or cold to the touch. Of course, the handling ring 58 may be of any suitable size or shape to accommodate being grasped by tongs or an insulated glove.

In the preferred embodiment of the invention shown in FIGS. 1-4, the edge shields 72 and 74, when connected together, also have a receptacle 60 adapted to receive and retain tube 64. The leads of thermocouple wires 36 may be passed through the tube 64 to the data recording module 20.

Coatings on the target 30 can be used to simulate the thermal characteristics of the process product. For example, in the food industry, the black body emissivity of food products such as cake and pizza should be approximated. Food products have a black body emissivity of about 0.8. Bright, polished metal surfaces will tend to reflect some radiative energy, while darker surfaces will tend to absorb radiative energy. Anodized aluminum surfaces having a dark gray color are preferred to approximate food products. Food products may contain a large amount of water, a highly absorbent material to radiation on the electromagnetic spectrum. Food products may also contain organic materials that form dark crusts upon heating, which tend to be highly absorptive to radiative heat energy.

The coating on the target 30 is preferably a hard coat material which is practically indelible and does not scratch off so that the target module 10 may be cleaned and does not have to be handled carefully to preserve the finish.

Instead of a coating, it is possible to finish the target 30 to a very slick polished finish by processing the target 30 with rocks in a vibrator. Rocks of different sizes and different coarseness produce a smooth polished surface on the target 30. Primarily for cleaning or aesthetic reasons, the same polished surface could be produced on the edge shield 70.

A food product, for example, has a black body emissivity of about 0.8 because the surface has a high water content. A dark painted or coated body has a similarly high emissivity. The black body emissivity of other process products could also be simulated with various coatings for the target 30.

As mentioned before, the temperature of the surrounding atmosphere within the heat exchange equipment is a piece of valuable information. As will hereinafter be described in detail, the calculation of the "h" value, also referred to as the heat transfer coefficient, the BTU per unit area per unit time and per unit change in temperature relative to the surrounding temperature is an important piece of information in comparing heat transfer rate profiles. Therefore, in the preferred embodiment of the invention, at least one surrounding atmosphere temperature sensor 80 is included in the heat transfer rate target module apparatus to measure the temperature of the surrounding atmosphere. In the preferred embodiment shown in FIGS. 1-4, the heat transfer rate target module includes a redundant surrounding atmosphere temperature sensor 82.

In the preferred embodiment of the invention, the surrounding atmosphere temperature sensors 80 and 82 comprise thermocouples 38 and 39, respectively, for the reasons hereinafter described in detail. If possible, the thermocouples 38 and 39 should be exposed directly to the surrounding atmosphere to achieve the greatest sensitivity and accuracy.

Therefore, the wire of thermocouples 38 and 39 must be supported in the surrounding atmosphere in the vicinity of the target 30. In the preferred embodiment, antenna 84 and 86 serve to support the thermocouples 38 and 39, respectively. In one embodiment, antenna 84 and 86 are manufactured from hollow tubular material of the type used for hypodermic needles to form an essentially straight stiff hollow tube. The thermocouples 38 and 39 can easily be threaded through the tubular antenna 84 and 86 and knots can be tied in the wires of the thermocouples 38 and 39 near the joined end of the thermocouple 38 and 39 so that the thermocouples 38 and 39 protrude from the ends of the antenna 84 and 86, respectively, but cannot pass back through the tubular antenna 84 and 86.

In the preferred embodiment of the invention, the antenna 84 and 86 may be attached to the data recording module 20, but the antennae 84 and 86 should move with the target module 10 and in the vicinity of the target module 10. As shown in FIGS. 1–4 of the drawing, the antenna 84 and 86 extend to either side of the target module 10 in a horizontal plane.

Though the antenna 84 and 86 should support the thermocouples 38 and 39, respectively, in the vicinity of the target 30, the thermocouples 38 and 39 should be spaced sufficiently far from the heat sink of the target module 10 so that the target module 10 does not substantially affect the temperature measurement of the surrounding atmosphere. Otherwise air jets or convection currents bouncing off the target module 10 could cause erroneous surrounding temperature data. Also the target module 10 may be such a large heat sink that it can actually change the temperature of the surrounding atmosphere. The data recording module 20 may be a smaller heat sink than the target module 10 so the surrounding atmosphere temperature sensors 80 and 82 may be attached to the data recording module 20.

Preferably the antenna 84 and 86 should extend in the same plane as the target module 10. Otherwise the height and footprint of the target module 10 may be so large that the target module 10 cannot be used in some heat exchange equipment. The target module 10 of the preferred embodiment illustrated in FIGS. 1–4 is more than eight (8) inches in diameter and about two (2) inches high because of the target mounting assembly 50. A smaller target module 10 would be required for some heat exchange equipment, such as some types of cookie ovens.

It is important that top surface 31 on top target 32 and bottom surface 33 on bottom target 34 be positioned approximately the same distance from upper and lower sources of heat as the upper and lower surfaces of the product to be processed. Thus, the thickness of target module 10 is preferably approximately equal to the thickness of the process product.

It is possible to orient the antenna 84 the redundant antenna 86 in any direction as long as the measurements are performed in a consistent manner. Therefore, once a particular orientation of the target module 10 and antenna 84 and 86 is employed, the same orientation should be used throughout gathering data and treating data.

Theoretically it preferable to construct the antenna 84 and 86 to measure the temperature along the center line of the target 30. For example, if the target module 10 is placed on a moving conveyer belt, as shown in FIG. 1 of the drawing, the antenna 84 and 86 position the thermocouples 38 and 39 into the heat exchange equipment such that the thermocouples 38 and 39 measure the temperature at the same point but at two different times, once before the target 30 measures the heat transfer in the vertical plane perpendicular to the direction of motion and one after the target 30 measures the heat transfer in the vertical plane perpendicular to the direction of motion. On the other hand, if the heat transfer rate target module shown in FIG. 1 of the drawing is oriented 90° about a vertical axis, then the two thermocouples 38 and 39 would measure temperatures in the surrounding atmosphere on either side of the target 30 at about the same time as the center of the target is measuring the heat transfer between the two thermocouples 38 and 39.

Depending on the heat exchange equipment, the temperatures measured by the two thermocouples 38 and 39 may be the same, but not necessarily. If the two thermocouples 38 and 39 register significantly different temperatures, other than perhaps a time delay, the difference may indicate a thermocouple problem or a problem with temperature zones in the heat exchange equipment. Of course, not all ovens, for example, have the same temperature throughout the zone.

If return air in an impingement oven is drawn to one side of the oven adjacent ends of entrance and exit openings into the oven, air flow throughout the cooking chamber may not be uniform. Different temperature readings at sensors 38 and 39 spaced from opposite sides of the centerline of the conveyor would indicate that air flow through air dispensing openings or air flow to an air return duct require adjustment or balancing to improve performance.

The various thermocouples used in the invention are well known in the art. Thermocouples are highly sensitive temperature sensors and can be calibrated to great accuracy and precision. At the same time, thermocouples are simple and highly resistant to heat. The thermocouple generally comprises two wires formed of different metals or alloys joined at one end. The wires can be joined with a little welded dot on the end. One wire is made out of one material and another wire is made out of a different material. In the preferred embodiment TYPE K thermocouples are used, which is a chromel-alumel thermocouple. TYPE K is easier to work with than some other thermocouples. For some applications TYPE K is better than TYPE J, which is an iron-constant thermocouple, because the iron rusts. But TYPE K is not the only type that will work; all types of thermocouples will work.

Usually, the exact orientation or location of the target 30 becomes less critical as the surface area of the target 30 is increased. The target 30 measures the average heat transfer per unit surface area. For example, a target 30 having a surface diameter of six (6) inches may not measure the heat transfer for individual jet effects in a hot-air impingement oven. The larger targets simulate a food product such as a loaf of bread or pie. In an alternative embodiment of the target, as will hereinafter be described, the surface area of the target 30 may be much smaller, small enough to form a discrete sensor that could measure the heat transfer of an individual jet in a hot-air impingement oven.

As previously mentioned, it is possible to manufacture smaller or larger targets 30. Or it may be desirable to manufacture a target module 10 with multiple small targets 30 disposed adjacent a single larger edge shield 70. For example, an array of one-quarter ($\frac{1}{4}$) inch diameter targets 30 may be used to measure the individual heat transfer effects of the several individual jets in a hot-air impingement oven. The edge effects must be eliminated by the same basic design of the invention, that is, by encircling the edges of the targets 30.

The uniform curve on the outer surfaces of the edge shield 70 minimizes convection turbulence or eddy effects that might result from sharp edges. But with the smaller target modules 10 that have multiple small targets 30, the edge effects of the edge shield 70 are relatively farther removed and hence less important. At some point other functionality features or even aesthetics may overcome the desirability for rounded surfaces on the edge shield 70, such as rounded surfaces 76 and 78.

As will hereinafter be described in more detail, the target module 10 can be used for measuring heat transfer rates in convection or combination convection and radiant heat ovens. An important feature of the target module 10 is the edge shield 70, which greatly reduces the edge effects on the target 30. The preferred embodiment of the target module 10 illustrated in FIGS. 1-4 can measure the generally vertical heat transfer in a convection or hot-air impingement oven, indicating the type of heat transfer conditions the top and bottom areas of a food product would be exposed.

The Data Recording Module

Figure 6:
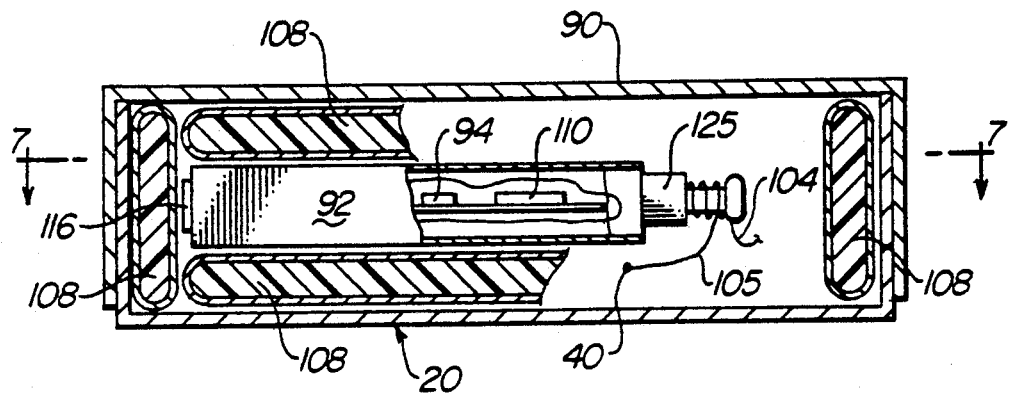
FIG. 6 is a cross-sectional view taken along line 6—6 of FIG. 3.
Figure 7:
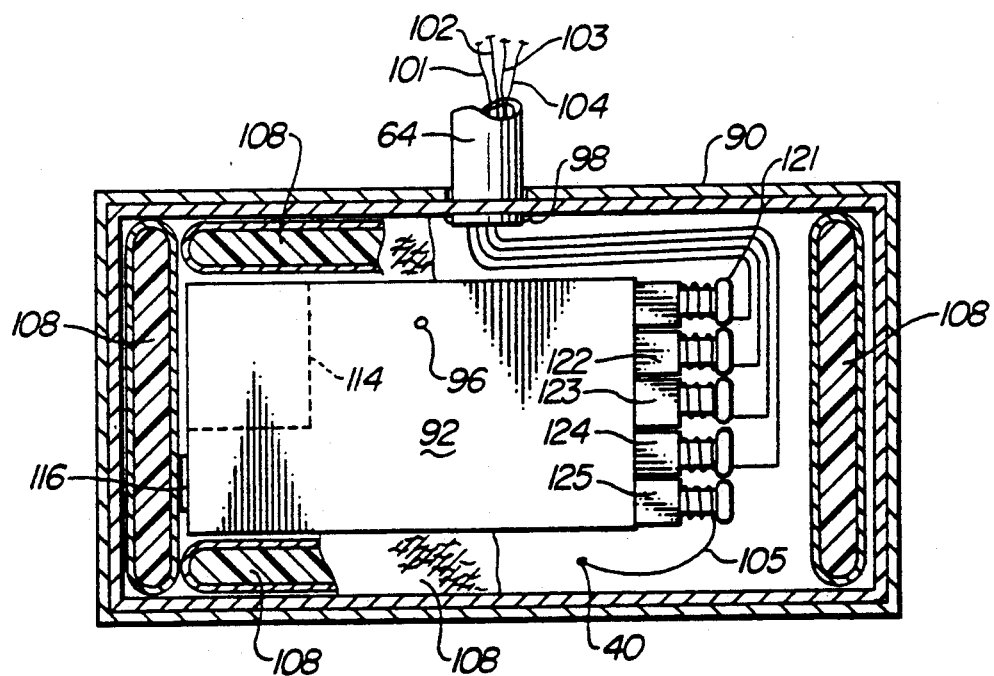
FIG. 7 is a cross-sectional view taken along line 7—7 of FIG. 6.

Referring now to FIGS. 6 and 7, the data recording module 20 generally comprises a thermally insulated case 90 having a receptacle therein for holding a data logger 92. The thermally insulated case 90 allows the data logger 92 to be sent into the heat exchange equipment with the target module 10. Welds 98 connect the tube 64 to the thermally insulated case 90. The interior of the tube communicates with the interiors of the thermally insulated case 90 and target mounting assembly 50 so that the thermocouples leads may pass therethrough to the data logger 92.

At a minimum, the data logger 92 should be able to record the temperature measurements of at least one target thermocouple 36 in at least one of the targets 30. In a preferred embodiment, the data logger 92 should be able to record the temperature measurements of the thermocouples 36 in multiple targets 30, and the temperature measurements of the surrounding atmosphere temperature thermocouples 38 and 39. In an even more preferred embodiment, the data logger 92 should be able to record the temperature within the insulated case 90 with another thermocouple 40.

The data logger 92 for recording this kind of temperature data is well known in the art and is commercially available from Electronic Controls Design, Inc. of Milwaukee, Oreg. under the registered trademark "M.O.L.E." for electronic data acquisition apparatus and prerecorded computer programs for measuring, recording, processing and displaying process parameters such as temperature profiles.

A "Baker's Super M.O.L.E. Thinline" from Electronic Controls Design, Inc. includes one set of five TYPE-K 0.005-inch thermocouples; one set of five TYPE-K 0.021-inch thermocouples; one IBM PC-compatible interface cable; two copies of software on 3-½ and 5-¼ inch discs; one non-contact magnetic starting wand; one 6-volt lithium battery; one aluminum carrying case; one hot box enclosure; one silver slipper; one pair of hot gloves; and one operator's manual. This kit is available as product No. SE30-0280-00.

Optional software entitled "DATA MANAGER SOFTWARE" is available as Product No. SY50-2887-60. Accessories available for use with the apparatus include a set of five 0.010 inch micro-size TYPE-K general purpose thermocouples with connectors and custom "collectors" attached as Product No. SY15-0216-10 and a "SUPER M.O.L.E. THINLINE" to 9-D IBM serial interface connector specified as Product No. SE00-2787-26.

The "SUPER M.O.L.E." provides a temperature signature profile from $-100°$ F. to $+1200°$ F., then translates that number into a "snap shot" of a specific time period. The accuracy of the equipment was within $1°$ F. at $100°$ F. The channel to channel compliance was within $1°$ F. (Operations manual of Super M.O.L.E. ©). The "M.O.L.E." recorder records at selected intervals and can be plugged into a personal computer to transfer the information to the computer. Using the "Data Manager Software" the recorded temperature profile which has been transferred to the computer can be displayed or printed as a graph indicating temperature in .F on a vertical axis and time in minutes on a horizontal axis.

"M.O.L.E." (Multi-Channel-Occurrent Logger Evaluator) is a registered trademark of Electronic Controls Design, Inc. The "M.O.L.E." data logger forms no part of the present invention except in combination with other structure disclosed herein.

The data logger 92 generally comprises a clock 94, data input leads, a data recording device 110, and a power supply 114. One example of a suitable data recording device 110 includes a "M.O.L.E.," which is the brand name of a commercially available data recording device. The "M.O.L.E." is suitable for this apparatus because the electronics have been specially protected with a thick layer of insulating material 118 that helps protect the delicate electronic circuitry and clock against temperatures up to $180°$ F.

The clock 94 is used to trigger when data should be recorded and the time the data was recorded so that data may be recorded at pre-set times. The data logger 92 can be pre-programmed to record data at any desired intervals after the data logger 92 is activated. The data logger 92 may also be programmed to delay beginning the data logging sequence for a period after activating the data logger 92 so that the data logger 92 may be placed within the receptacle of the thermally insulated case 90, the heat transfer rate target module can be placed in the heat exchange equipment, and the heat exchange process of the heat exchange equipment may be initiated.

A magnetic sensitive dot 96 on the data logger is used to activate the data logger 92. The M.O.L.E. is provided with a magnetic wand (not shown) that starts the M.O.L.E. when the magnetic end of the wand is passed over the magnetic sensitive dot 96. Other types of switches may be employed to activate the data logger 92.

In the preferred embodiment of the invention, the data recording device 110 includes at least one computer memory chip which stores digital data. The thermocouple temperature sensors provide analog data. Therefore, in the preferred embodiment of the invention, an analog-to-digital converter 112 is electronically interposed between the data input leads of the thermocouple wires and the data recording device 110.

The data on a computer chip is volatile, meaning that when the power supply 114 is removed, the data is lost. In the preferred embodiment of the invention, the power supply 114 comprises a battery pack. A battery power supply allows the data recording module 20 to operate independently of a fixed power supply. Therefore, the data must be transferred to another permanent memory device before the battery of the power supply 114 is disconnected or exhausted. The memory chip of the data recording device 110 should be able to store at least 200 data points for each of five different data inputs, along with the time at which the data points were measured.

The data input leads 101, 102, 103, 104, and 105 connect with the leads of the thermocouples 36 from the top target 32, 37 from the bottom target 34, 38 from surrounding atmosphere temperature sensor 80, 39 from redundant surrounding atmosphere temperature sensor 82, and 40 from the interior of the thermally insulated case 90, respectively.

The various leads of the thermocouples 36, 37, 38, 39, and 40 are separately wound around the connectors 121, 122, 123, 124, and 125, respectively, which correspond to data input leads 101, 102, 103, 104, and 105, respectively. The connectors 101-105 provide a suitable spindle shape for wrapping extra thermocouple wire.

The connectors also store extra thermocouple wire because thermocouples sometimes break. Most of the problems occur at the end of the thermocouple where the two wires are welded or joined together. The thermocouples 38 and 39 of the surrounding atmosphere temperature sensors are particularly vulnerable to breaking because the joined ends of the thermocouples are totally exposed. To repair a thermocouple, simply cut off the old joint or weld dot at the end to the thermocouple, pull out a little extra wire from the appropriate connector and join the wires to form a new thermocouple connection.

The serial computer interface 116 may be connected with a standard serial cable to the serial port on a computer. When the serial interface 116 is plugged into the serial port on the computer, it is possible to download the data from the data recording device 110 of the data logger 92 into the memory system of the computer. Then a program in the computer processes the measured data as desired. The most effective way to use the data is in conjunction with the mass and thermal properties of the target 30 so that the heat transfer and the rate of heat transfer can be calculated. The results can be tabulated or graphed as desired.

The thermally insulated case 90 should be adequately insulated to keep the interior of the thermally insulated case 90 below about 180° F. The electronic circuitry of the data recording device 92 could probably withstand somewhat higher temperatures, but the batteries of the power supply 114 may not. The insulation 108 in the data recording module 20 may be formed of a fiberglass or other suitable material to provide the highest insulating factor possible to reduce the size of the data recording module 20. The longer and hotter the time in the oven, the more effective the insulation must be and the more insulation 108 is required. In the preferred embodiment of the invention, a thermocouple 40 measures the temperature inside the thermally insulated case 90.

If desired, the data logger 92 can be programmed at a remote location far from the heat exchange process equipment, sent with the apparatus by overnight mail, used to record data with a target module 10, and returned to the remote location. The data can be retrieved and analyzed at the remote location.

Method of Operation

The invention includes the development of the computations and computer software for calculating the heat transfer, q, the heat transfer per unit area, $q_a$ and the rate of heat transfer per unit area, r, as described in Equations 1-4. The computer software could include calculus computations to take into account the fact that the thermal capacity of the target 30 may vary with the temperature of the target 30. As previously mentioned, it has also been discovered that the heat transfer coefficient, h, can be a useful value for measuring and standardizing heat transfer processes. The heat transfer coefficient, h, can be calculated as follows:

$$h = (r) \frac{\text{(calibration period)}}{\text{(Avg. Atm. Temp.} - \text{Avg. Target Temp.)}} \quad \text{Eq. 5}$$

where r is obtained from Equation 3, the calibration period is a stand time period for which h is measured, "Avg. Atm. Temp." is the average temperature of the surrounding atmosphere over the measurement time of the particular experiment, and "Avg. Target Temp" is the average temperature of the target 30 over the measurement time of the particular experiment.

To simplify the computations, a constant, k, can be calculated for each target 30 so that:

$$h = \frac{(k)\text{(calibration period)}}{\text{(actual time) (Avg. Atm. Temp.} - \text{Avg. Target Temp.)}} \quad \text{Eq. 6}$$

where $$k = \frac{\text{(mass) (thermal capacity)}}{\text{(area)}} \quad \text{Eq. 7}$$

and where mass is the mass of the target 30, thermal capacity is the thermal capacity of the target 30, and area is the exposed surface area of the target 30. The constant, k, is particular to each particular target. The calibration period may be incorporated into the constant if desired. The calibration period may be any convenient period, two minutes for example. But preferably the calibration period should approximately equal the typical actual measurement time. The most accurate measurements and values are used to calculate the constant.

The h-value is for the target 30. The h-value should approximate these values for process products and give consistent, scientific data to compare operating conditions and heat exchange devices. In the preferred embodiment of the invention shown in FIGS. 1-4, the h values can be measured separately for the top and the bottom targets 33 and 34.

We have determined that for an aluminum target having a mass of about 300 grams, an h-value of about 5 to 10 is in the range of a typical convection oven. For a hot-air impingement oven the h-value may be 30 or higher.

Figure 8:
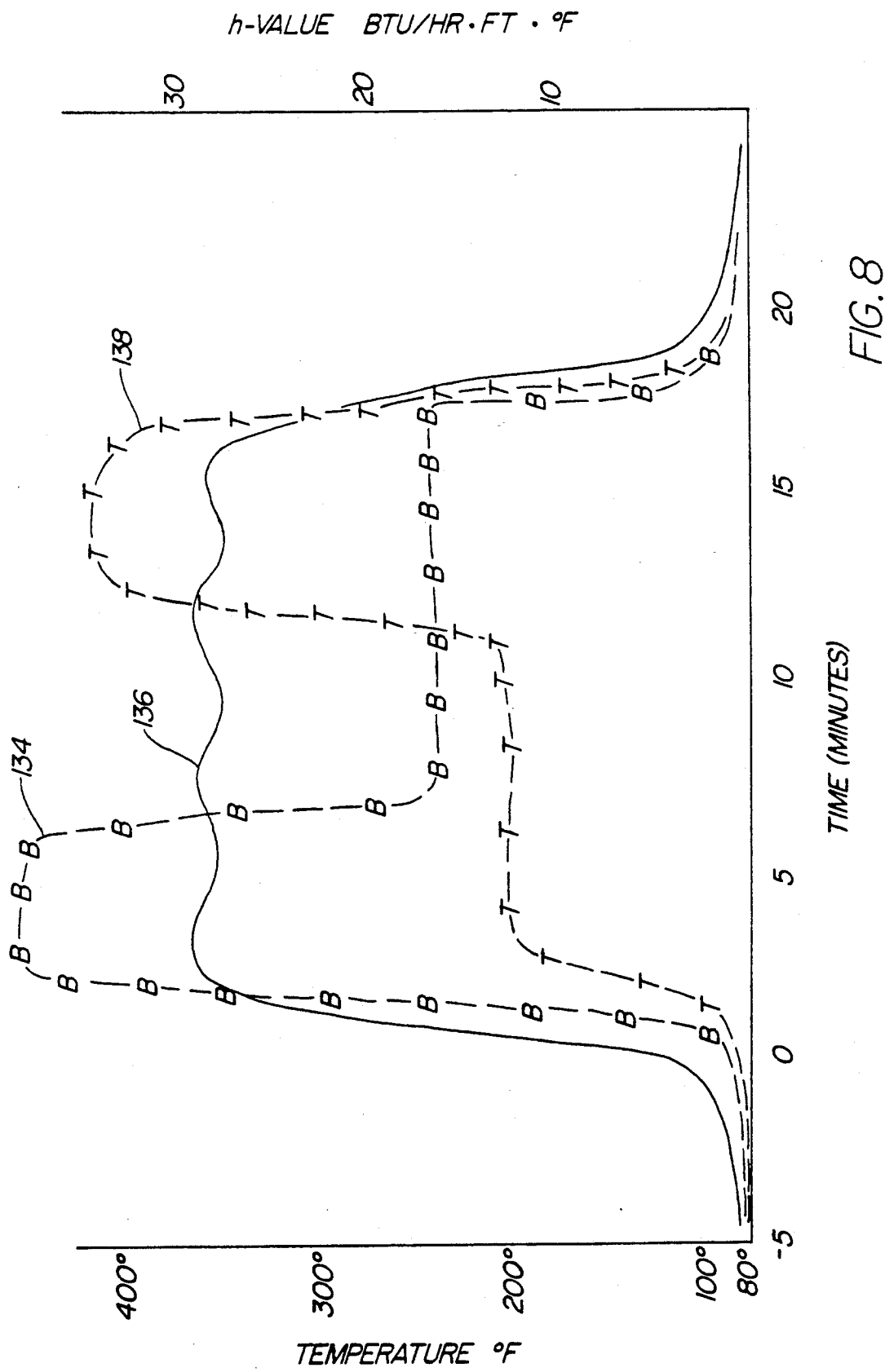
FIG. 8 is a graphic representation of an example of a time profile of the rate of heat transfer for the process of baking a cake as measured by a heat transfer target module.

The data from the data logger can be tabulated as successive temperatures or graphed as temperature vs. time. Knowing the mass and thermal capacity of the target 30, the H-value (Equation 1), $q_a$-value (Equation 2), r-value (Equation 3), or h-value (Equation 5 or 6) may all be easily calculated from the temperature and time data. FIG. 8 is a graph illustrating an h-value vs. time profile of a particular baking oven. The graph of FIG. 8 is an example of the type of data that the heat transfer rate target module 100 of the invention can provide for the baking oven. The first calculus derivative of the changes in temperatures vs. time or h-value vs. time can also be useful.

FIG. 8 shows the h-value vs. time for the top target 32, shown by line 132, and the bottom target 34, shown by line 134. The top and bottom heat transfer rates can be modified by changing baffles, fan motor speed, or other flow control devices in the convection oven or the jets of a hot-air impingement oven. FIG. 8 also shows the temperature vs. time in the oven, shown by line 136. The temperature does not show where the heat transfer is taking place.

The graph illustrated in FIG. 8 is a graphic representation of data recorded by the heat transfer rate module while it was being carried by a conveyor through an oven of the type disclosed in Smith U.S. Pat. No. 4,831,238 filed Sept. 22, 1989, entitled "HIGH VOLUME FORCED CONVECTION TUNNEL OVEN", the disclosure of which is incorporated herein by reference in its entirety for all purposes. A high volume force convection tunnel oven of the type disclosed in Smith U.S. Pat. No. 4,831,238 is generally designated by the numeral 210 in FIGS. 9 and 10 of the drawing.

Cooking apparatus 210 generally comprises a plurality of spaced cabinets 212a, 212b, and 212c. Each cabinet 212 has a cooking chamber 244 therein defined between front wall 216, back wall 218, top 220, bottom 222 and spaced end walls 224 and 226. A conveyor 230 transports food products 235 through an inlet opening 225 and an exit opening 227 in each cabinet 212. Conveyor 230 preferably comprises a wire mesh conveyor belt driven by a variable speed drive motor 231 positioned adjacent the discharge end of the conveyor to rotate conveyor 230 at a controlled speed.

Front wall 214 is provided with a door 236 while back wall 218 is provided with a door 238.

A generally horizontally disposed distribution chamber 240 is formed between top 220 of the cabinet 212 and a generally horizontally disposed wall 242 having an air intake opening 244' formed therein.

Two generally vertically disposed plenums 252 and 254 are formed adjacent a back wall 218 of the cabinet, a first plenum 252 being formed between vertical walls 245 and 246 and a second plenum 254 being formed between vertical wall 246 and the back wall 218 of the cabinet. A gate 250 is pivotally secured adjacent the upper end of the central vertical wall 246 between the first plenum 252 and the second plenum 254 and is movable from the position illustrated in full outline in FIG. 10 to the position illustrated in dashed outline for adjusting air flow from distribution chamber 240 through the vertically disposed plenums 252 and 254.

Upper fingers 270 are suspended from vertically movable hanger members such as rods 256 having lower ends secured to a generally rectangular shaped frame secured to each of the upper fingers 270. Each hanger 256 is moved vertically by suitable elevating means such as hydraulically actuated cylinders 258.

Figure 10:
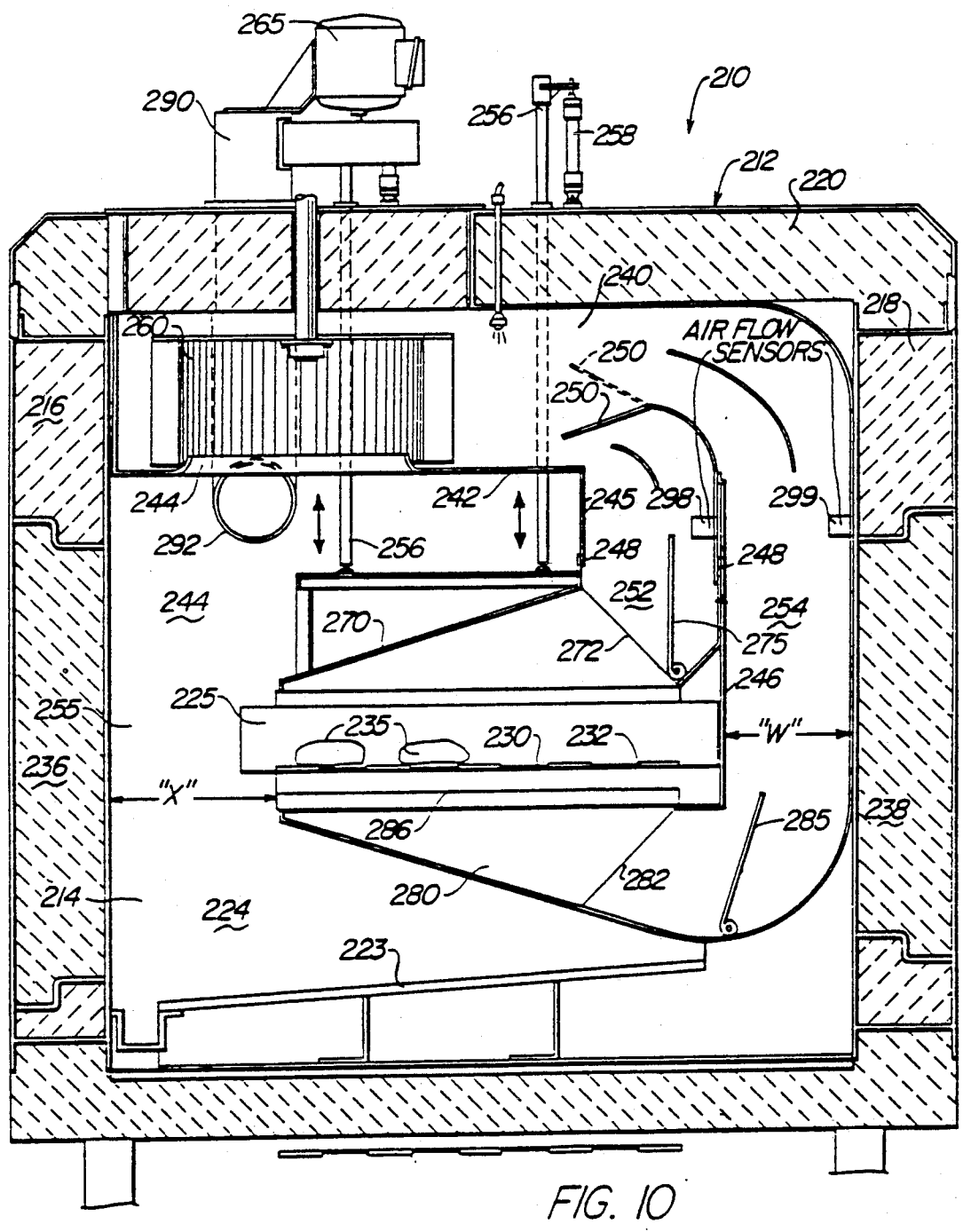
FIG. 10 is a cross-sectional view taken along line 10—10 of FIG. 10.

As best illustrated in FIG. 10, the central plenum wall 246 and the front plenum wall 245 each has a sliding joint 248 formed therein permitting adjustment of the elevation of the array of upper dispensing ducts 270 relative to upper chamber 240.

A fan or blower 260 is rotatably disposed in chamber 230 and is driven by a variable speed blower motor 265 mounted on top wall 220.

A plurality of horizontally spaced upper air dispensing ducts 270 are secured to spaced openings 272 which communicate with the interior of plenum 252 for dispensing air delivered through plenum 252 onto the upper surface of food products 235 carried by conveyor 230. A plurality of lower plenums 280 are spaced longitudinally of cooking compartment 244 and communicate with openings 282 in wall 246 of plenum 254 such that air flowing through plenum 254 enters lower dispensing ducts 280 and is dispensed onto the lower surface of food products 235 carried on conveyor 230.

Dampers 275 and 285 are preferably adjustably positioned adjacent openings 272 and 282 communicating with plenums 252 and 254 to provide independent adjustment of air flow through each of the spaced upper dispensing ducts 270 relative to each of the other upper dispensing ducts 270 and to provide adjustment of flow from each of the lower dispensing ducts 280 relative to each of the other lower dispensing ducts 280. Gate 250 and dampers 275 and 285 are of substantially identical construction, except that dampers 275 and 285 are shorter. For example, if the spacing between interior end walls 224 and 226 is six feet, gate 250 is approximately six feet long, while dampers 275 and 285 may be only six inches long. It should be readily apparent that gate 250 can be manipulated for adjusting flow of air from chamber 240 to plenums 252 and 254 while dampers 275 and 285 can be manipulated for adjusting flow through individual ducts 270 and 280 for precisely adjusting the sequence and intensity of heat transfer to upper and lower surfaces of food product 235. An air heating element such as gas fire heater 292 delivers heated air into cooking compartment 244 in each cabinet 212. The heated air is preferably dispensed adjacent the intake opening of blower 260.

For example, to cause the best bake on a bread dough can be challenging. Not only does the temperature and heat transfer rate of the oven determine the quality of the baked product, but also the complex chemistry of baking dough. The heat transfer rate target module can be used to accurate determine the heat transfer rates of baking ovens. If the same dough recipe is used with the same quality of ingredients, the heat transfer rate target module makes it possible to produce a quality baked bread with a degree of consistency never before achievable. The exact heat exchange profiles can be studied and modified as necessary.

The h-value vs. time profile for the bottom target 34 shows that heat is initially put into the bottom of the cake for about five minutes to heat the pan and to cause the bread to rise and accomplish most of the baking chemistry. Later the h-value is reduced from the bottom direction but increased from the top direction, shown by the h-value vs. time profile for the top target 32 during the time interval from about five to about 10 minutes. The higher heat transfer toward the end of the baking process during the time interval from about ten to fifteen minutes browns the crust and creates the highly aromatic organic products.

Figure 11:
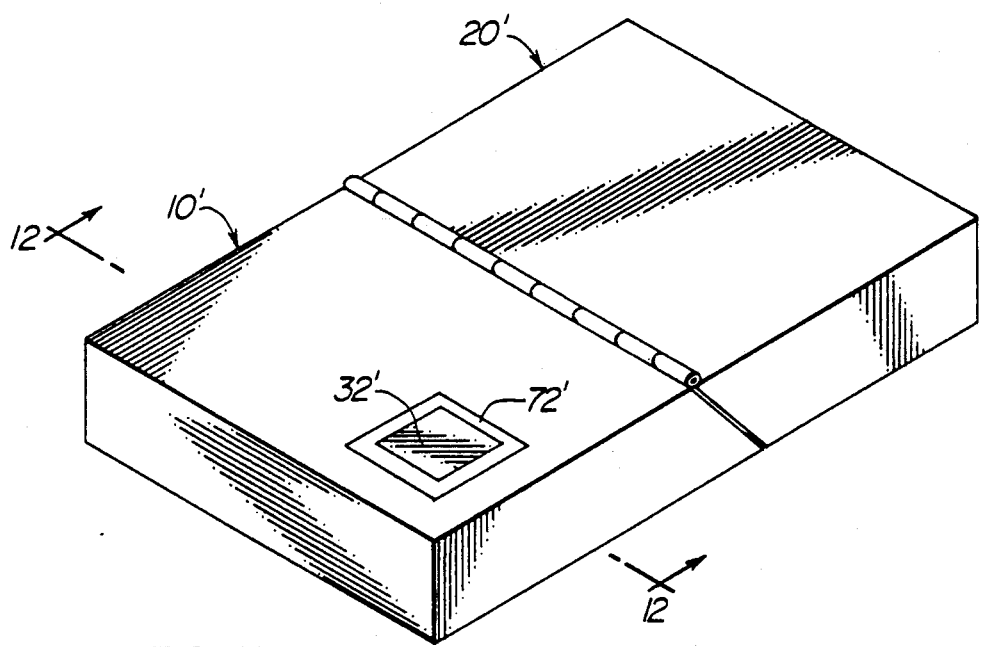
FIG. 11 is a perspective view of a second embodiment.
Figure 12:
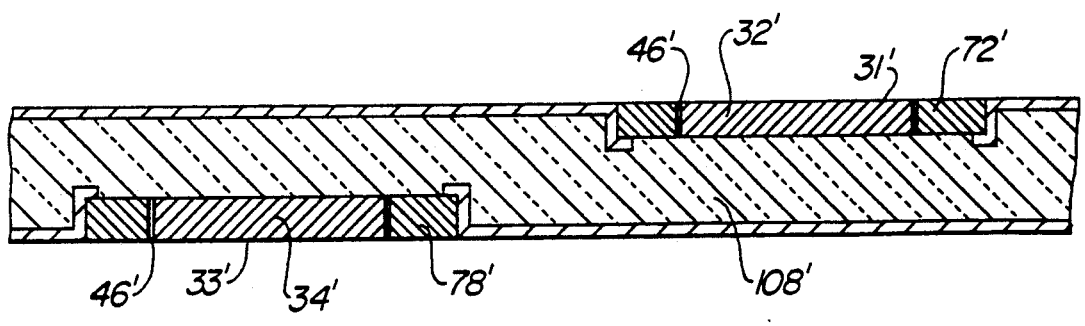
FIG. 12 is a cross-sectional view taken substantially along line 12—12 of FIG. 11.

A second embodiment of the invention is illustrated in FIGS. 11 and 12 of the drawing. The apparatus is similar to that hereinbefore described except that the top target plate 32' and bottom target plate 34' are laterally offset relative to each other. A top edge shield 72' extends around the periphery of extends around the periphery of a bottom target plate 34'. The interior of the carrier is filled with a suitable insulation material 108' such that heat is delivered to the upper surface 31' of the top target plate 32' and to the lower surface 33' of the lower target plate 34'. The gaps 46' extend around the periphery of each of the target plates.

In the embodiment of the invention illustrated in FIG. 11 and 12 of the drawing targets 32' and 34' are mounted adjacent of one end of a carrier while the data logger 20' is mounted in the opposite end of the carrier, a hinged cover being formed on the carrier to provide access to the data logger.

It should be readily apparent that more than one target plate 31' may be employed over the upper surface of the carrier while a plurality of bottom target plates 34' may be employed over the bottom of the carrier to provide additional inputs.

Numerous alterations, modifications, and changes can be made in the design of the invention disclosed herein without departing from the scope and spirit of the invention defined by the claims.

The invention having been described, what is claimed is:

1. An apparatus for determining the heat transfer between a surface and the environment surrounding the surface, the apparatus comprising:
    (a) a target, said target formed of a material having a known mass and known thermal capacity, said target having at least one exposed surface for energy exchange with the environment of said target, and said target having at least one non-exposed surface;
    (b) an edge shield, said edge shield formed of the same material as said target and having the same thermal capacity as said target, said edge shield completely surrounding at least said non-exposed surfaces of said target that are adjacent said exposed surface of said target, but said edge shield not physically contacting said target such that said target and said edge shield form a narrow gap therebetween whereby conductive heat transfer between said edge shield and said target is minimized and whereby edge effects on said target are minimized;
    (c) means for supporting said target adjacent said edge shield such that said narrow gap is formed therebetween, said means for supporting said target adjacent said edge shield minimizing conductive heat transfer between said target and said edge shield; and
    (d) a means for measuring the temperature of said target.

2. The apparatus of claim 1 wherein said target is formed of aluminum.

3. The apparatus of claim 1 wherein said target is cylindrical and has a diameter of about six inches and an length of about one-quarter inch.

4. The apparatus of claim 3 wherein said edge shield has a thickness of about one-quarter inch.

5. The apparatus of claim 1 wherein the surfaces of said edge shield that are positioned adjacent to said non-exposed surfaces of said target have about the same surface area as said non-exposed surfaces of said target.

6. The apparatus of claim 1 wherein said target is covered with a hard coating, said hard coating being dark in color so that the surface is more absorptive to incident radiation than a bright surface whereby said target may simulate more absorptive process products.

7. The apparatus of claim 1 wherein the exposed surface of said target is highly reflective to incident radiation to simulate highly reflective process products.

8. The apparatus of claim 1 wherein the gap between said target and said edge shield is generally between about 1/1000th and about 25/1000th inch.

9. The apparatus of claim 1 wherein said edge shield minimizes the edge effects on said target by presenting a substantially uniform surface at the periphery of said exposed surface of said target.

10. The apparatus of claim 1 wherein said edge shield has rounded surfaces distal to the surfaces that are positioned adjacent to said target so that said edge shield minimally effects the convection currents near said target.

11. The apparatus of claim 1 wherein said means for supporting said target adjacent said edge shield comprises several positioning pins mounted to said edge shield.

12. The apparatus of claim 1 wherein said means for measuring the temperature of said target is a thermocouple.

13. The apparatus of claim 12 wherein said means target has a hole to accommodate the joined end of said thermocouple.

14. The apparatus of claim 1 wherein said means for measuring the temperature of said target is connected to a data recording device.

15. An apparatus for measuring the heat transfer and rate of heat transfer in thermal exchange equipment, the apparatus comprising a target module and a data recording module, wherein said target module comprises:
    (a) a heat sink, said heat sink being formed of a material having a known mass and a known thermal capacity;
    (b) an edge shield, said edge shield being formed of a the same material as said heat sink and having the same thermal capacity as said heat sink, said edge shield being configured to surround said heat sink such that said heat sink has at least one exposed surface and non-exposed surfaces said non-exposed surfaces being adjacent said exposed surface;
    (c) a means for supporting said heat sink adjacent said edge shield while minimizing the direct physical contact between said heat sink and said edge shield such that a narrow gap is formed between said heat sink and said edge shield; and
    (d) a means for sensing the temperature of said heat sink; and wherein said data recording module comprises:
    (a) a data recording device;
    (b) a clock, said clock being electrically connected to said data recording device;
    (c) at least one data input lead, said means for measuring the temperature of said heat sink being connected to said data input lead, said data input lead being electrically connected to said data recording device;
    (d) a power supply, said power supply being electrically connected to said clock and said data recording device;

whereby said data recording module may record any changes in the temperature of said heat sink as said heat sink is processed in the thermal exchange equipment.

16. The apparatus of claim 15 wherein said data recording module is physically connected to said target module.

17. The apparatus of claim 15 wherein said data recording module additionally comprises a thermally insulated case for holding and insulating therein said data recording device, said clock, said data input lead, and said power supply.

18. The apparatus of claim 15 having at least two data input leads.

19. The apparatus of claim 18 further comprising a means for measuring the temperature surrounding said target module, said means for measuring the temperature surrounding said target module being connected to one of said input leads of said data recording module.

20. The apparatus of claim 15 wherein said means for measuring the temperature surrounding said target module is a thermocouple supported by an antenna, said antenna being connected to said target module or said data recording module.

21. The apparatus of claim 15 wherein said heat sink is cylindrical.

22. The apparatus of claim 21 wherein said edge shield surrounds said heat sink such that both planar surfaces of said cylindrical heat sink are exposed surfaces, thereby allowing said heat sink to measure the combined heat transfer of both surfaces.

23. The apparatus of claim 15 wherein said target module has at least two heat sinks, a means for measuring the temperature of each heat sink, at least two data input leads, said data input leads being electrically connected between said means for measuring the temperatures of said heat sinks and said data recording device.

24. A process for controlling heat transfer between a food product and a heat transfer media, wherein the food product is simulated by a target means, the method comprising the steps of:
   determining the temperature of a target means at selected time intervals;
   determining the heat transfer rate between the heat transfer media and the target means at selected time intervals;
   comparing the determined heat transfer rate at each time interval to recorded data to determine the variance between the determined heat transfer rate at each time interval and the recorded data; and
   controlling the heat transfer media to adjust the heat transfer rate at each time interval in the heat transfer media to maintain the variance between the recorded data and the heat transfer rate at each selected time interval within a predetermined range.

25. The method of claim 24, the step of determining the rate of heat transfer between the heat transfer media and the target means comprising the steps of: determining the rate of heat transfer between the heat transfer media and the top of the target means; and determining the rate of heat transfer between the heat transfer media and the bottom of the target means.

26. The method of claim 24, with the addition of the step of determining ambient temperature in the heat transfer media.

27. The method of claim 24, the step of comparing the variance comprising the steps of: forming a graphic representation of the heat transfer rate between the heat transfer media and the target means at selected time intervals; and comparing the graphic representation to a recorded graphic representation of the rate of heat transfer between a heat transfer media and a target means.

28. A method of cooking a food product in a pan comprising the steps of: applying heat to the top surface of the food product and to the bottom surface of the pan such that the heat transfer rate to the bottom of the pan is greater than the heat transfer rate to the top surface of the food product for a predetermined time interval; adjusting the rate of heat transfer to the bottom of the pan independently of the rate of heat transfer to the top of the food product; maintaining predetermined heat transfer rates to the top of the food product and to the bottom of the pan for a predetermined time interval; adjusting the heat transfer rate to the top of the food product independently of the rate of heat transfer to the bottom of the pan for a predetermined time interval; recording the heat transfer rate to the top surface of the food product and to the bottom surface of the pan at selected time intervals; comparing the recorded heat transfer rate at specified time intervals to measured heat transfer rates at selected time intervals in a second oven; and adjusting the heat transfer rates at the respective time intervals in the second oven to maintain the variance between the heat transfer rates at the selected time intervals within a specified range relative to the heat transfer rates as depicted by the recorded data.

29. The method of claim 28, the step of recording the respective heat transfer rates comprising the step of: printing a graph of the rate of heat transfer to the top surface of the food product, the rate of heat transfer to the bottom surface of the pan and ambient temperature in the heat transfer chamber at selected time intervals to form a graph.

* * * * *

UNITED STATES PATENT AND TRADEMARK OFFICE
CERTIFICATE OF CORRECTION

PATENT NO. : 5,161,889

DATED : November 10, 1992

INVENTOR(S) : Donald P. Smith; Jarald E. High; John R. Norris

Figure 9:
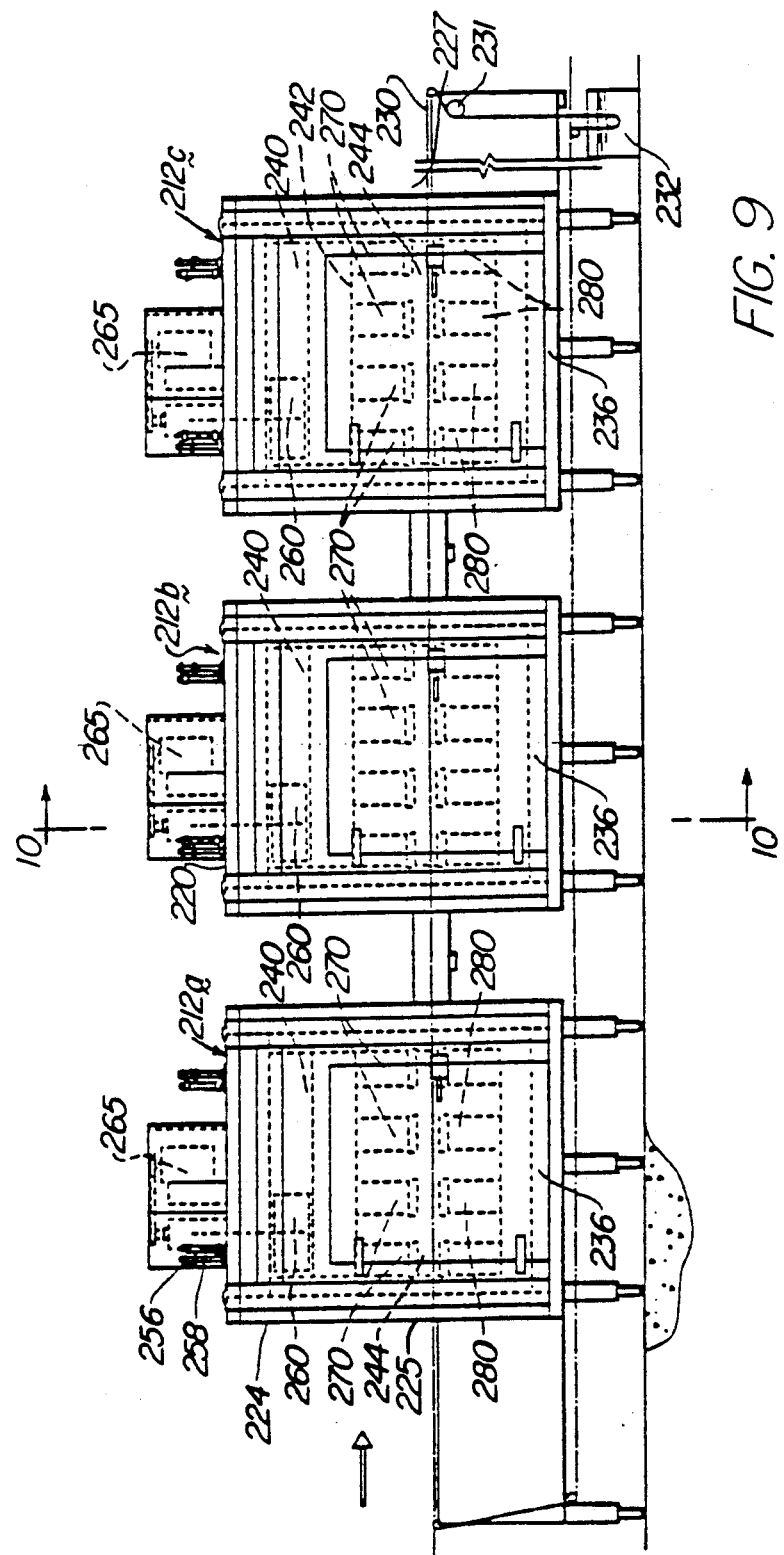
FIG. 9 is an elevational view of an oven in which the module may be used.

It is certified that error appears in the above-identified patent and that said Letters Patent is hereby corrected as shown below:

Col. 3, line 34, delete "FIG. 10" and in lieu thereof insert -- FIG. 9 --

Col. 5, line 62, delete "boy" and in lieu thereof insert -- body --

Col. 6, line 15, delete "$q_a$ = a/area, or" and in lieu thereof insert -- $q_a$ = q/area, or --

Col. 7, line 19, after "shaped" insert -- , --

Col. 7, line 59, after "30" insert -- . --

Col. 14, line 18, delete ".F" and in lieu thereof insert -- °F --

Col. 18, line 62, after "of" insert -- top target plate 32' and a bottom edge shield 78' --

Col. 20, line 17, delete "means"

Signed and Sealed this

Eleventh Day of January, 1994

Attest:

BRUCE LEHMAN

*Attesting Officer*   *Commissioner of Patents and Trademarks*